(12) United States Patent
Crosby

(10) Patent No.: US 8,679,350 B1
(45) Date of Patent: Mar. 25, 2014

(54) ACIDIC MINE WATER REMEDIATION

(75) Inventor: David Crosby, Whittington (GB)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/978,592

(22) PCT Filed: Apr. 30, 2012

(86) PCT No.: PCT/EP2012/057928
§ 371 (c)(1),
(2), (4) Date: Jul. 8, 2013

(87) PCT Pub. No.: WO2012/156198
PCT Pub. Date: Nov. 22, 2012

(30) Foreign Application Priority Data

May 13, 2011 (GB) .................................. 1107955.5

(51) Int. Cl.
*C02F 1/28* (2006.01)
*C02F 1/62* (2006.01)
*C02F 101/20* (2006.01)
*C02F 103/10* (2006.01)

(52) U.S. Cl.
CPC . *C02F 1/285* (2013.01); *C02F 1/62* (2013.01); *C02F 2101/20* (2013.01); *C02F 2103/10* (2013.01); *Y10S 210/912* (2013.01); *Y10S 210/913* (2013.01)
USPC ............................ 210/688; 210/912; 210/913

(58) Field of Classification Search
CPC ........ C02F 1/285; C02F 1/64; C02F 2101/20; C02F 2101/203; C02F 2101/206; C02F 2101/22; C02F 2103/10
USPC .......................................... 210/688, 912, 913
See application file for complete search history.

(56) References Cited

U.S. PATENT DOCUMENTS

| | | |
|---|---|---|
| 3,464,920 A | 9/1969 | Pirson et al. |
| 4,408,030 A | 10/1983 | Marko |
| 5,667,694 A | 9/1997 | Cody et al. |
| 5,695,882 A | 12/1997 | Rosenberg |
| 5,876,609 A | 3/1999 | White et al. |
| 6,077,439 A | 6/2000 | El-Ammouri et al. |
| 6,296,760 B1 | 10/2001 | Petty et al. |
| 6,478,870 B2 | 11/2002 | Marko |
| 6,656,360 B2 | 12/2003 | Jones et al. |
| 7,759,434 B2 | 7/2010 | Funk et al. |
| 2008/0164215 A1* | 7/2008 | Tavlarides et al. ............ 210/688 |
| 2011/0132845 A1* | 6/2011 | Edmiston ...................... 210/688 |

FOREIGN PATENT DOCUMENTS

| | | |
|---|---|---|
| DE | 3523541 A1 | 1/1987 |
| DE | 4232177 A1 | 3/1994 |

OTHER PUBLICATIONS

English Language Abstract of DE 4,232,177, Mar. 1994, Derwent, Acc. No. 1994-110205, one page.*
English Language Abstract of DE 3,52,3541, Jan. 1987, Derwent, Acc. No. 1987-015204, one page.*

* cited by examiner

*Primary Examiner* — Matthew O Savage
(74) *Attorney, Agent, or Firm* — Catherine U. Brown

(57) ABSTRACT

A process for treating acidic mine drainage water to remove heavy metal ions is described in which acidic mine drainage water is contacted with direct process residue gel.

15 Claims, 3 Drawing Sheets

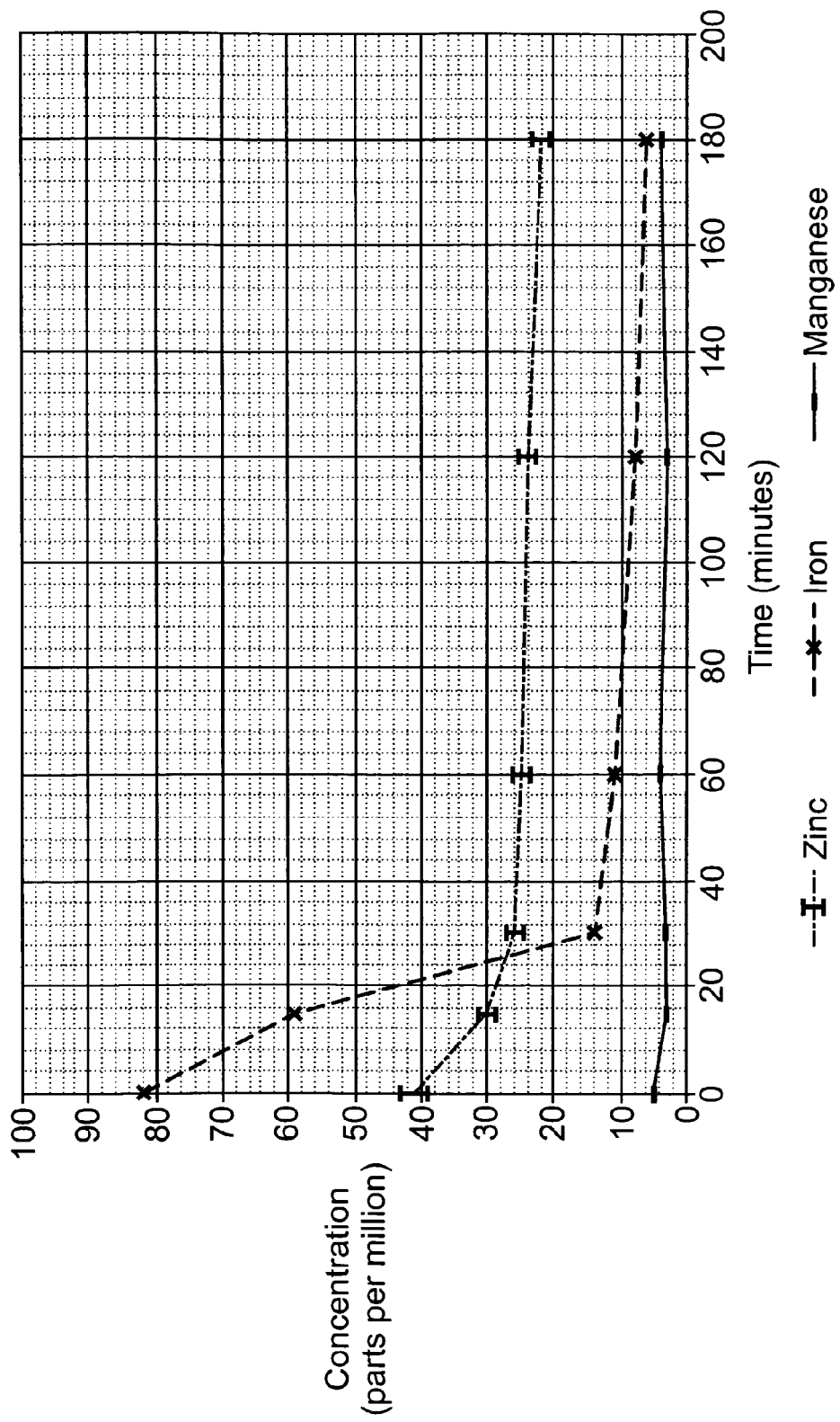

ACIDIC MINE WATER REMEDIATION

This application is a U.S. national stage filing under 35 U.S.C. §371 of PCT Application No. PCT/EP2012/057928 filed on 30 Apr. 2012, currently pending, which claims the benefit of GB Patent Application No. 1107955.5 filed 13 May 2011 under 35 U.S.C. §120. PCT Application No. PCT/EP2012/057928 and GB. Patent Application No. 1107955.5 are hereby incorporated by reference.

This invention relates to mine water remediation and in particular to the treatment of acidic mine drainage water to remove heavy metal ions. The treatment is particularly applicable to acidic mine drainage water from an abandoned or closed mine, but can also be used to treat acidic mine drainage water from a working mine.

Acid mine drainage is mainly caused by oxidation of pyrite (iron sulphide mineral). Pyrite oxidises to produce acidic water often having a pH below 3. The presence of water promotes oxidation of the pyrite. When a mine, for example a coal mine, iron ore mine or other metal ore mine, is abandoned, there is usually a build-up of water because pumping of water from the mine has ceased. Pyrite is exposed in many mines, and the build-up of water produces a drainage stream of acidic water. When the pH of the water is sufficiently low, metal deposits within the mine may dissolve into the acidic water. This acidic metal laden solution can then overflow the mine and pollute the local environment. Reduction of pH in water leads to less dissolved oxygen and reduces enzyme activity, while certain microorganisms such as Sphagnum flourish removing essential ions from other organisms. The decrease in pH also results in the precipitation of iron salts as $Fe(OH)_3$ (ochre) causing a red stain and acting as a site for co-precipitation of other metals. The heavy metal ions present in the mine water may for example include ions of iron, manganese, chromium, copper, zinc, cadmium and lead, amongst others.

Various treatments have been suggested for mine water remediation. These can be active treatments, in which a neutralising agent is added to the source of the acid mine drainage or to a stream which has been polluted, or passive treatments. Neutralising agents which have been suggested for active remediation of acid mine drainage include calcium carbonate, calcium oxide or hydroxide, ammonia, sodium hydroxide or sodium carbonate. In passive treatments the acid mine drainage is passed through drains, channels or ponds, generally of limestone, or to aerobic or anaerobic wetlands.

EP-A-765842 describes contacting an aqueous system containing heavy metal contaminants with an organically modified smectite clay.

WO99/19523 describes removing metal ions from a fluid stream by placing a liquid having an affinity for the metal ions on a mat of hollow wicking fibres, and directing the fluid stream through the mat into contact with the liquid along the channels within the hollow wicking fibres.

U.S. Pat. No. 5,695,882 describes producing a material for extracting heavy metal ions from aqueous solutions, for example lead from drinking water, by silanizing the hydrated surface of a solid extraction material with a silane, and reacting the silanized surface with a polyamine.

U.S. Pat. No. 6,296,760 describes a device for removing metal ions such as cadmium, copper, nickel, lead or zinc ions from water comprising a nonporous polymer membrane for capturing the metal ions and a hydrophobic sequestration medium contained by the membrane which changes the metal ions into a complexed, non-mobile metal species.

In a process according to the present invention for treating acidic mine drainage water to remove heavy metal ions, the acidic mine drainage water is contacted with direct process residue gel.

Direct process residue gel is derived from the production of methylchlorosilanes. Methylchlorosilanes are commercially produced by what is commonly called "the direct process", in which silicon metal is reacted with methyl chloride ($CH_3Cl$) in the presence of a catalyst. The reaction takes place in a fluid bed reactor in which finely ground silicon metal powder is fluidised by passing methyl chloride gas there through at a temperature of between 200° C. and 500° C. A by-product of the direct process is direct process residue (DPR). DPR comprises between 50-90% the higher boiling point methylchlorodisilanes (boiling point higher than methylchlorosilanes) with the general formula $Si_2(CH_3)_xCl_y$, where x+y=6. The remainder of the material substantially comprises silmethylenes $SiCH_2Si(CH_3)_jCl_k$ where j+k=6 and higher boiling polysilanes, where the general formula is $Si_n(CH_3)_mCl_p$ where m+p=6+(2(n−2)). The remainder of the direct process residue comprises a variety of materials, typically including iron, silicon metal, copper, organic materials, and salts (e.g. calcium chloride), DPR is a chemically active, hazardous material, whose activity must be reduced prior to transportation and/or disposal. Thus, once separated from the other reaction products, DPR is neutralised with an alkaline aqueous solution and optionally dewatered, resulting in a gel-solids mixture, referred to hereinafter as "direct process residue gel" or "DPR gel". Methods for neutralising DPR are described for example in U.S. Pat. No. 4,408,030 and U.S. Pat. No. 5,876,609.

The invention includes the use of direct process residue gel to reduce the heavy metal ion content of acidic mine drainage water.

DPR gel is a hydrolysis product of the constituents of DPR (i.e. the hydrolysis product of e.g. silicon compounds such as disilanes, larger polysilanes and silmethylenes) which are hydrolysed into a highly cross-linked gel. The precise composition of the DPR gel produced as described above may vary dependent on the relative amounts of the constituents in the DPR from which the gel is obtained but typically the major components of DPR gel are the products of the hydrolysis of disilanes (the amount of disilanes in direct process residue may for example be from 50 to 80 wt %). The DPR gel, that is the gel-solids mixture produced after dewatering, usually has a water content in the range 35 to 60% by weight.

The DPR gel can be used in the form in which it is produced as described above or can be modified, for example by the separation of ungelled solids and/or by removal of salts. The higher boiling point silicon compounds can be filtered before they are hydrolysed; this removes ungelled solid materials such as silicon metal, iron and copper derived from the direct process reaction vessel. The DPR gel can be washed after it is formed to remove at least partly soluble salts such as calcium chloride. We have however found DPR gel as produced as a commercial by-product in the form of a solid highly cross-linked structure is highly effective in removing heavy metal ions from mine water, and the DPR gel is preferably used without filtration or washing.

The DPR gel can be contacted with the acidic mine drainage water in any of a number of different methods. The acidic mine drainage water or a stream contaminated with acidic mine drainage water can be passed through a bed of DPR gel. The contaminated water can for example be pumped out of the mine and passed (pumped or trickled) through the DPR gel, either as a packed cartridge of DPR gel or a loose bed of DPR gel. The loose bed of DPR gel can be used similarly to the way filter aid powders are deployed in industrial filtration using a plate-and-frame filter press.

In an alternative process the mine causing acidic mine drainage water contamination (usually an exhausted coal or metal mine) is surrounded by a lining filled with DPR gel so that rainwater entering the mine has to pass through the DPR gel on its path to the environment. A large 'catch-all' lining can be dug around the contamination zone and filled with the DPR gel. Rainwater enters the mine and picks up contamination but in its path back into the environment it has to pass through the DPR gel, where the contaminants are removed. The heavy metal contaminants may be any heavy metal ions detrimental to the environment and present in mine water for example ions of iron, manganese, chromium, copper, zinc, cadmium and lead and mixtures thereof.

In a further alternative the acidic mine drainage water or a stream contaminated with acidic mine drainage water can be fed to a pond lined with direct process residue gel. A single pond or a plurality of such ponds arranged in series can be used. Water leaving the pond, or the last of a series of ponds, passes to the environment.

Alternatively the DPR gel can be added to a stream of acidic mine drainage water or a stream contaminated with acidic mine drainage water. The DPR gel can be added to the flowing stream or the stream can be fed to a pond to which the DPR gel is added. The DPR gel can for example be added at 0.1 to 40 g per liter of acidic mine drainage water. Typical amounts of DPR gel may be 1 to 20 g per liter to treat heavily polluted acidic drainage water from a disused mine or 0.1 to 2 g per liter to treat less polluted acidic drainage water or drainage water from an active mine.

The mine drainage water which has been treated with DPR gel can be tested for acidity and/or for heavy metal ion content. Such testing may be carried out continuously or on samples taken intermittently. Once the water is tested and shown to meet standards, it is returned to the environment.

We have found DPR gel to be highly effective in removing heavy metal ions from mine water; it is much more effective than clay minerals such as zeolites. We believe that the alkaline nature of the DPR gel causes metals dissolved in the acidic mine drainage water to precipitate out. Furthermore, the DPR gel is an extremely porous solid and thus has a high surface area to trap the metals. The DPR gel can readily be ground to a desired particle size if required, for example when adding the DPR gel to the mine drainage water or for forming a filtration cartridge of DPR gel.

The invention is illustrated by the following Example, in which parts and percentages are by weight. The Example includes FIGS. 1 to 3 of the accompanying drawings:

FIG. 3 is a graph of the concentration of zinc, iron and manganese in mine drainage water against time after addition of zeolite in a comparative experiment.

EXAMPLE

In a laboratory test, 8 g DPR gel was added to 200 mL acidic mine drainage water from an abandoned metal ore mine in Cornwall, England. This mine has highly contaminated drainage water of pH 2.47 containing 30 parts per million (ppm) zinc, 34 ppm manganese and 78 ppm iron. The DPR gel was a gel of water content 45 to 50 wt. %, produced by hydrolysing with lime solution higher boiling point organochlorosilanes produced in the manufacture of methylchlorosilanes by the direct process in which silicon metal was reacted with methyl chloride. The DPR gel was mixed with the acidic mine drainage water in a tumbling mill for 3 hours. Samples were taken for analysis after 15 min, 30 min 1 hour, 2 hours and 3 hours. The analysed samples were filtered and the metal content was determined by atomic adsorption spectrophotometry.

Figure 1:
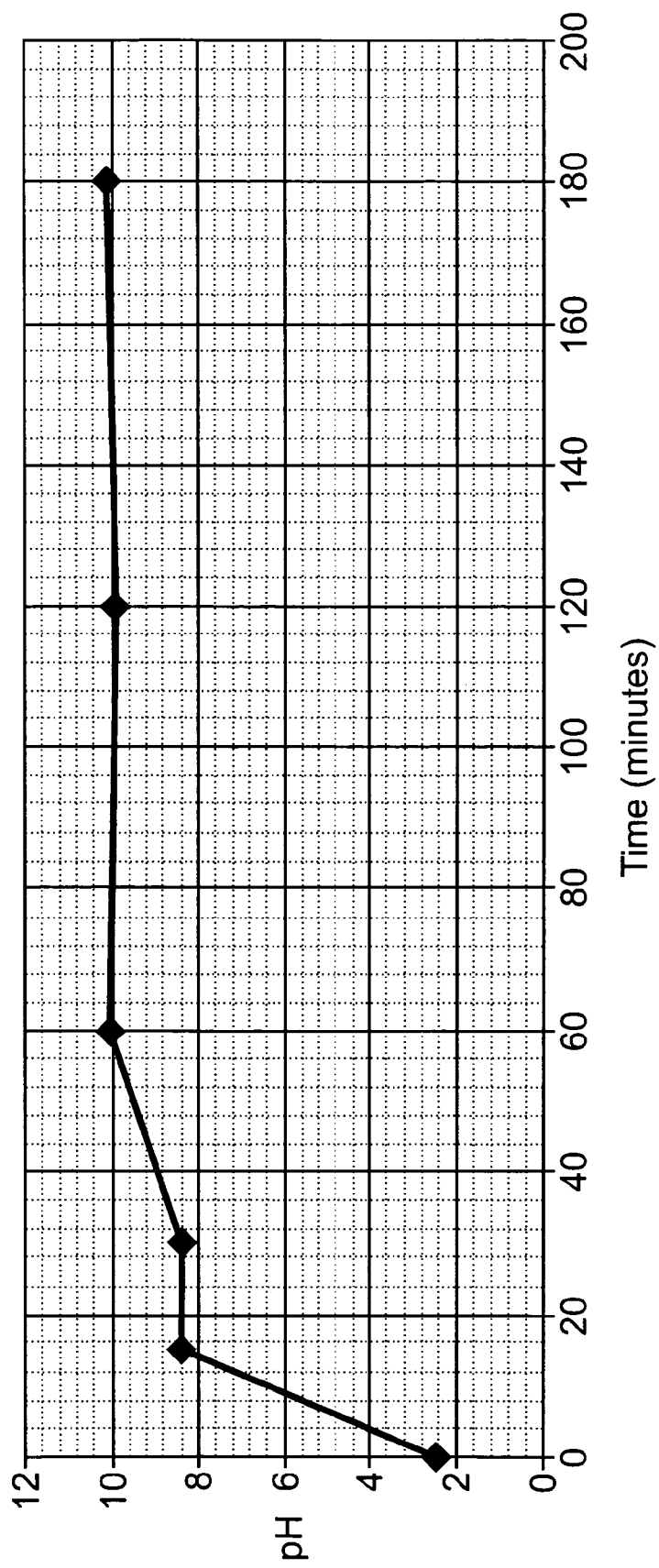
FIG. 1 is a graph of the pH of mine drainage water against time after addition of DPR gel.

The effect of the DPR gel on the pH of the acidic mine drainage water is shown in FIG. 1, which is a graph of the pH of the mine drainage water against time after addition of the DPR gel. It can be seen that the pH rises above pH 8 within ten minutes of addition of the DPR gel, and after an hour reaches a steady pH of about 10.

By comparison, when the same amount of the zeolite clinoptilolite is added to the acidic mine drainage water from the abandoned metal ore mine, the pH only rises to 2.81 after an hour and 2.87 after 3 hours.

Figure 2:
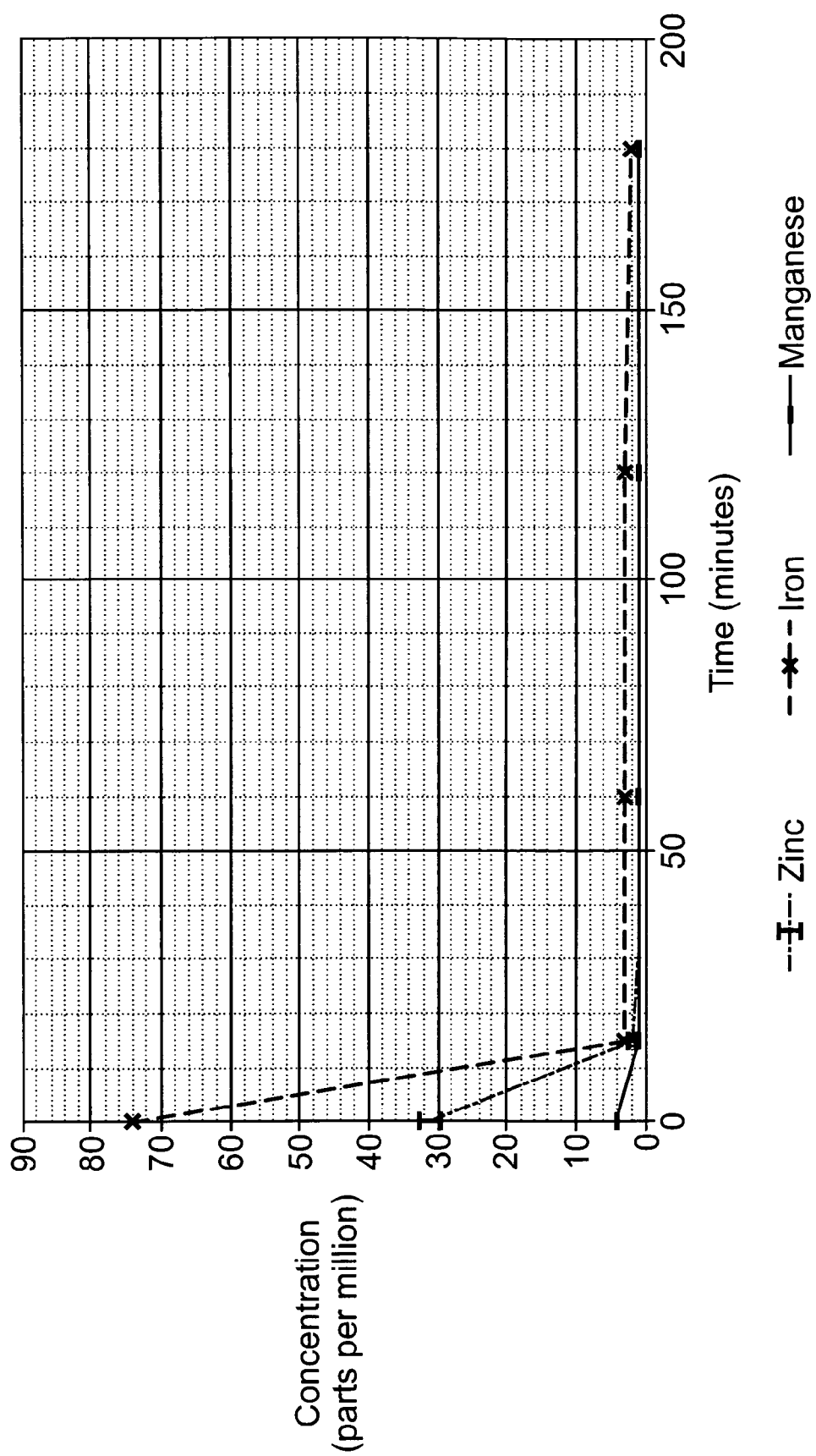
FIG. 2 is a graph of the concentration of zinc, iron and manganese in mine drainage water against time after addition of DPR gel.

The effect of the DPR gel on the heavy metal content of the acidic mine drainage water is shown in FIG. 2, which is a graph of the concentration of zinc, iron and manganese in the mine drainage water against time after addition of the DPR gel. It can be seen that the concentration of each of these metals is reduced to below 5 ppm within 15 minutes and remains below this level.

By comparison, FIG. 3 shows the concentration of zinc, iron and manganese in the mine drainage water against time after addition of zeolite (clionptilolite). The zeolite has a considerable effect in removing metals from the water, but the concentration of iron remains above 25 ppm and the concentration of zinc above 15 ppm even after 150 minutes. The DPR gel is clearly more effective than zeolite in remediation of the mine drainage water.

The invention claimed is:

1. A process for treating acidic mine drainage water or a stream contaminated with acidic mine drainage water to remove heavy metal ions therefrom, comprising the steps of:
    providing a direct process residue gel by reacting silicon metal with methyl chloride in the presence of a catalyst to produce methylchlorosilanes and direct process residues including methylchlorodisilanes, simethylenes, and polysilanes, separating the methylchlorosilanes from the direct process residue, and hydrolyzing the direct process residues to produce the direct process residue gel; and
    contacting the acidic mine drainage water or the stream contaminated with acidic mine drainage water with the direct process residue gel to remove heavy metals therefrom.

2. A process according to claim 1, wherein the contacting step includes passing acidic mine drainage water or the stream contaminated with acidic mine drainage water through a bed of the direct process residue gel.

3. A process according to claim 2, wherein the contacting step includes packing the bed of direct process residue gel in a cartridge and pumping the acidic mine drainage water through the cartridge.

4. A process according to claim 2, wherein the step of contacting includes trickling the acidic mine drainage water or the stream contaminated with acidic mine drainage water through a loose bed of the direct process residue gel.

5. A process according to claim 2, wherein the step of contacting includes surrounding a mine creating the acidic mine drainage water with a lining filled with the direct process residue gel so that rainwater entering the mine has to pass through the direct process residue gel on its path out of the mine to an environment surrounding the mine.

6. A process according to claim 1, wherein the contacting step includes feeding the acidic mine drainage water or the stream contaminated with acidic mine drainage water to a pond lined with direct process residue gel.

7. A process according to claim 1, wherein the step of contacting includes adding the direct process residue gel to a stream of the acidic mine drainage water or the stream contaminated with acidic mine drainage water.

8. A process according to claim 1 wherein the heavy metal ions include iron, manganese, chromium, copper, zinc, cadmium and lead and mixtures thereof.

9. The process of claim 1, where the direct process residue gel is added at 0.1 to 40 g per liter of acidic mine drainage water.

10. The process of claim 9, where the direct process residue gel is added at 1 to 20 g per liter, and the acidic mine drainage water is heavily polluted acidic drainage water from a disused mine.

11. The process of claim 9, where the direct process residue gel is added at 0.1 to 2 g per liter, and the acidic mine drainage water is less polluted acidic drainage water or drainage water from an active mine.

12. The process of claim 1, wherein the direct process residue gel has a water content in the range 35 to 60% by weight.

13. The process of claim 1, wherein hydrolyzing the direct process residue includes neutralizing the direct process residue with an alkaline aqueous solution to form the direct process residue gel followed by dewatering the direct process residue gel.

14. The process of claim 13, further comprising separation of un-gelled solids from the direct process residue by filtering, and removing salts from the direct process residue gel by washing.

15. The process of claim 13, wherein the direct process residue is not filtered and the direct process residue gel is not washed before the step of contacting.

* * * * *